US010893869B2

(12) United States Patent
Choubey

(10) Patent No.: US 10,893,869 B2
(45) Date of Patent: Jan. 19, 2021

(54) THIN WALL CONSTRUCTIONS FOR VASCULAR FLOW DIVERSION

(71) Applicant: Covidien LP, Mansfield, MA (US)

(72) Inventor: Animesh Choubey, Chino, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/469,276

(22) Filed: Mar. 24, 2017

(65) Prior Publication Data

US 2017/0273692 A1    Sep. 28, 2017

Related U.S. Application Data

(60) Provisional application No. 62/313,051, filed on Mar. 24, 2016.

(51) Int. Cl.
| | |
|---|---|
| *A61B 17/12* | (2006.01) |
| *A61F 2/92* | (2013.01) |
| *A61F 2/91* | (2013.01) |
| *A61F 2/82* | (2013.01) |
| *A61F 2/07* | (2013.01) |
| *A61B 17/00* | (2006.01) |

(52) U.S. Cl.
CPC .. *A61B 17/12172* (2013.01); *A61B 17/12022* (2013.01); *A61B 17/12036* (2013.01); *A61B 17/12109* (2013.01); *A61B 17/12113* (2013.01); *A61B 17/12118* (2013.01); *A61F 2/91* (2013.01); *A61F 2/92* (2013.01); *A61B 2017/00592* (2013.01); *A61F 2/07* (2013.01); *A61F 2002/823* (2013.01)

(58) Field of Classification Search
CPC ......... A61F 2002/823; A61B 17/12022; A61B 17/12036; A61B 17/12109; A61B 17/12113; A61B 17/12118; A61B 17/12168; A61B 17/12172; A61B 2017/00592
See application file for complete search history.

(56) References Cited

U.S. PATENT DOCUMENTS

| | | | |
|---|---|---|---|
| 5,354,295 | A | 10/1994 | Guglielmi et al. |
| 5,669,931 | A | 9/1997 | Kupiecki et al. |
| 5,951,599 | A | 9/1999 | McCrory |
| 6,309,367 | B1 | 10/2001 | Boock |
| 6,602,261 | B2 | 8/2003 | Greene et al. |

(Continued)

FOREIGN PATENT DOCUMENTS

| | | |
|---|---|---|
| JP | 2004016668 | 1/2004 |
| JP | 2004016668 A | 1/2004 |

(Continued)

*Primary Examiner* — Sarah A Simpson
(74) *Attorney, Agent, or Firm* — Fortem IP LLP; Katrina Henrikson

(57) ABSTRACT

Devices that can be delivered into a vascular system to divert flow are disclosed herein. According to some embodiments, devices are provided for treating aneurysms by diverting flow. A flow-diverting device can comprise, for example, a frame and mesh immovably attached to and extending over a portion of the frame. The mesh can include a plurality of pores that are sized to inhibit the flow of blood through the frame into an aneurysm to a degree sufficient to lead to thrombosis and healing of the aneurysm when the device is positioned in a blood vessel and adjacent to the aneurysm.

18 Claims, 7 Drawing Sheets

(56) References Cited

U.S. PATENT DOCUMENTS

| | | |
|---|---|---|
| 6,605,101 B1 | 8/2003 | Schaefer et al. |
| 6,878,384 B2 | 4/2005 | Cruise et al. |
| 7,229,461 B2 | 6/2007 | Chin et al. |
| 7,601,160 B2 | 10/2009 | Richter |
| RE42,625 E | 8/2011 | Guglielmi |
| 8,043,326 B2 | 10/2011 | Hancock et al. |
| 8,425,541 B2 | 4/2013 | Masters et al. |
| 8,470,013 B2 | 6/2013 | Duggal et al. |
| 8,715,317 B1 | 5/2014 | Janardhan et al. |
| 8,906,057 B2 | 12/2014 | Connor et al. |
| 8,915,950 B2 | 12/2014 | Cam et al. |
| 8,940,003 B2 | 1/2015 | Slee et al. |
| 9,180,031 B2 | 11/2015 | Vogel et al. |
| 9,211,202 B2 | 12/2015 | Strother et al. |
| 9,486,224 B2 | 11/2016 | Riina et al. |
| 9,603,732 B2 | 3/2017 | Ma et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 2001/0000797 A1 | 5/2001 | Mazzocchi |
| 2001/0001835 A1 | 5/2001 | Greene et al. |
| 2003/0004567 A1* | 1/2003 | Boyle .................... A61F 2/91 |
| | | 623/1.16 |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2005/0209678 A1 | 9/2005 | Henkes et al. |
| 2005/0267511 A1 | 12/2005 | Marks et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0248871 A1* | 11/2006 | Johnson .................... A61F 2/01 |
| | | 57/58.83 |
| 2006/0287701 A1* | 12/2006 | Pal .................... A61F 2/013 |
| | | 623/1.11 |
| 2007/0100426 A1 | 5/2007 | Rudakov et al. |
| 2007/0175536 A1 | 8/2007 | Monetti et al. |
| 2007/0191924 A1 | 8/2007 | Rudakov |
| 2010/0023105 A1 | 1/2010 | Levy et al. |
| 2010/0144895 A1 | 6/2010 | Porter |
| 2011/0009950 A1 | 1/2011 | Grandfield et al. |
| 2011/0137405 A1 | 6/2011 | Wilson et al. |
| 2011/0184452 A1 | 7/2011 | Huynh et al. |
| 2011/0184453 A1 | 7/2011 | Levy et al. |
| 2012/0209311 A1* | 8/2012 | Grandfield .......... A61B 17/221 |
| | | 606/200 |
| 2012/0316632 A1 | 12/2012 | Gao |
| 2013/0274866 A1 | 10/2013 | Cox et al. |
| 2014/0012307 A1 | 1/2014 | Franano et al. |
| 2014/0014530 A1* | 1/2014 | Lin .................... A61F 2/86 |
| | | 205/660 |
| 2014/0058420 A1 | 2/2014 | Hannes et al. |
| 2014/0200653 A1* | 7/2014 | Elmaleh ................ A61L 31/022 |
| | | 623/1.16 |
| 2014/0296965 A1* | 10/2014 | Poor .................... A61F 2/915 |
| | | 623/1.15 |
| 2014/0316012 A1 | 10/2014 | Freyman et al. |
| 2014/0371734 A1 | 12/2014 | Truckai |
| 2015/0150672 A1* | 6/2015 | Ma .................... A61B 17/12031 |
| | | 606/200 |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |

FOREIGN PATENT DOCUMENTS

| | | |
|---|---|---|
| JP | 2005532887 | 11/2005 |
| JP | 2006026423 | 2/2006 |
| JP | 2006095095 | 4/2006 |
| JP | 2006095095 A | 4/2006 |
| WO | 2011066962 A1 | 6/2011 |
| WO | 2012087301 A1 | 6/2012 |
| WO | 2017074411 A1 | 5/2017 |
| WO | 2018051187 A1 | 3/2018 |

* cited by examiner

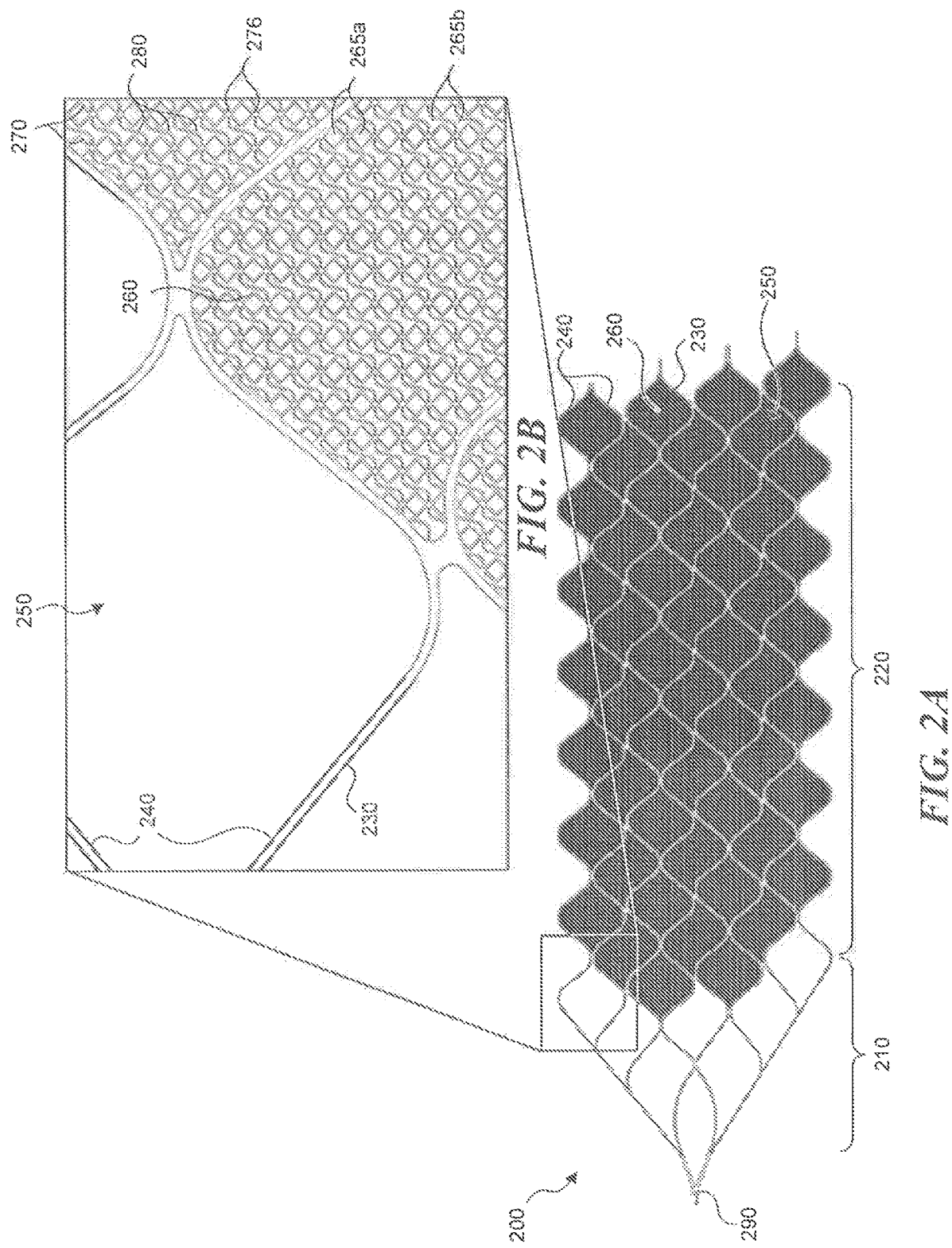

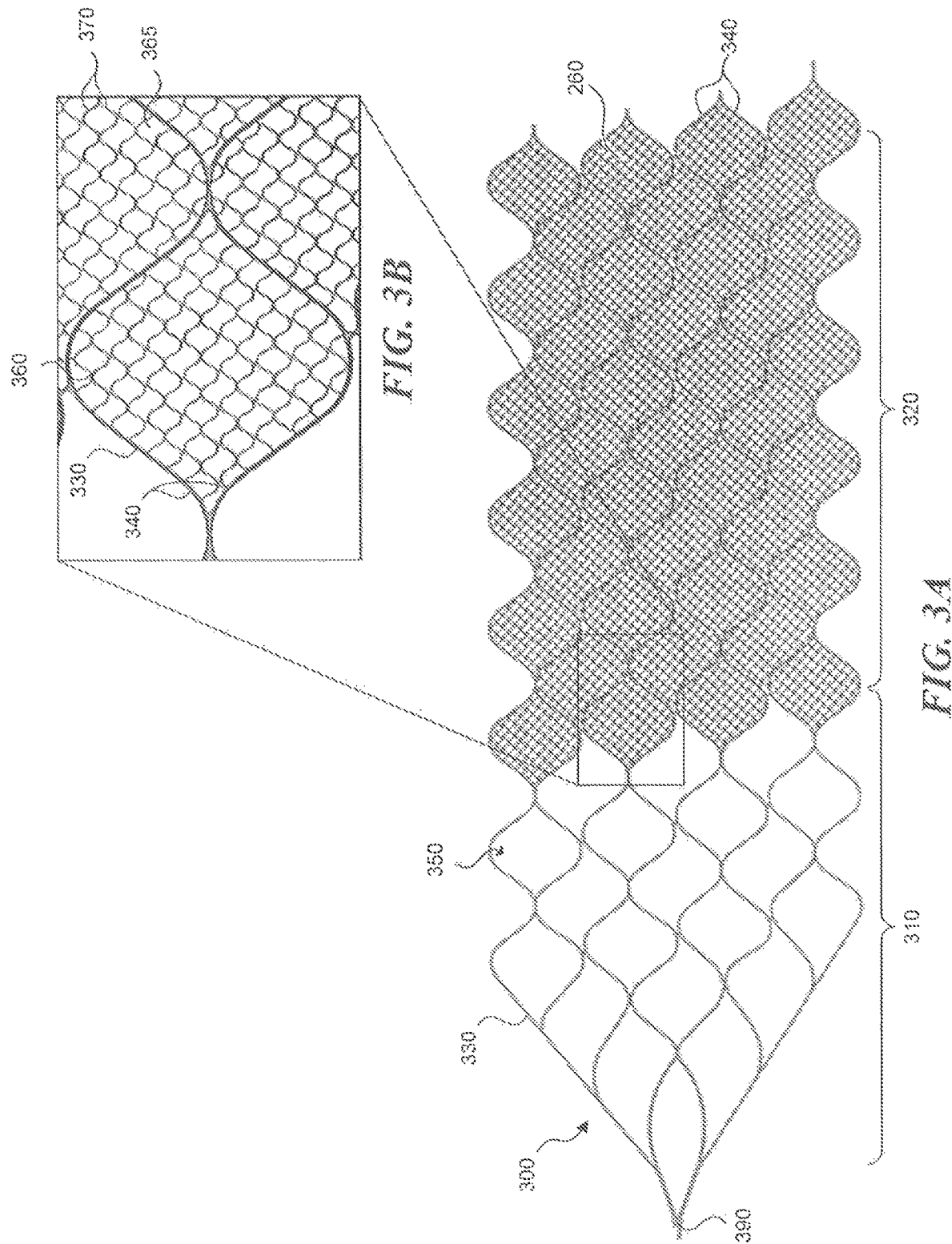

THIN WALL CONSTRUCTIONS FOR VASCULAR FLOW DIVERSION

CROSS-REFERENCE TO RELATED APPLICATION

The present application claims the benefit of and priority under 35 U.S.C. § 119(e) to U.S. Provisional Patent Application No. 62/313,051, filed Mar. 24, 2016, which is incorporated herein by reference in its entirety.

TECHNICAL FIELD

The present technology relates generally to methods and devices for diverting blood flow in a blood vessel, and particularly to inhibiting blood flow into an aneurysm. Some embodiments of the present technology relate to flow-diverting devices including a plurality of interconnected struts.

BACKGROUND

Aneurysms are an abnormal bulging or ballooning of a blood vessel that can result from the vessel wall being weakened by disease, injury, or a congenital abnormality. Aneurysms have thin, weak walls and have a tendency to rupture, which can lead to stroke, death, disability, etc. One method of treating aneurysms includes inserting a flow-diverting stent or braid into a parent vessel that includes the aneurysm to be treated. Such stents or braids can be inserted into a vessel in a collapsed state, positioned next to the neck of the aneurysm, and expanded into apposition with the vessel wall. If the stent or braid has a sufficiently low porosity, it can function to block the flow of blood through the device and into the aneurysm to induce embolization of the aneurysm.

However, some aneurysms—and especially cerebral aneurysms—are located in small and tortuous portions of the vasculature. Current designs for flow-diverting stents or braids have difficulty achieving a snug fit across the neck of the aneurysm if the parent vessel is curved, twisted, or forked. For example, current designs generally suffer from crimping or kinking when positioned in such tortuous vessels. This can make it more difficult to position a flow-diverting device and can cause the device to have an inadequate porosity as the device is expanded within the vessel. Also, current designs often undesirably block blood flow to branching or secondary vessels that are close to the aneurysm. Accordingly, there exists a need for improved flow-diverting devices for treating aneurysms.

SUMMARY

Expandable devices can be delivered into vascular system to divert flow. According to some embodiments, expandable devices are provided for treating aneurysms by diverting flow. A flow-diverting expandable device can comprise a plurality of struts and configured to be implanted in a blood vessel. The expandable device can be expandable to an expanded state at an aneurysm. The expandable device can have at least a section for spanning the neck of the aneurysm and a plurality of pores located between the struts. The expandable device can have a sidewall and a plurality of pores in the sidewall that are sized to inhibit flow of blood through the sidewall into an aneurysm to a degree sufficient to lead to thrombosis and healing of the aneurysm when the expandable device is positioned in a blood vessel and adjacent to the aneurysm.

According to some embodiments, the expandable device can include a frame comprising a plurality of interconnected frame struts forming frame cells and a flow-diverting mesh extending over at least a portion of a length and circumference of the frame. The frame and the flow-diverting mesh can be of a single material and/or monolithic piece.

In some embodiments, a delivery system for treating an aneurysm can comprise a microcatheter configured to be implanted into a blood vessel, a delivery wire extending within the microcatheter and having a distal segment, and the expandable device extending distally from the delivery wire distal segment.

In some embodiments, a flow-diverting device can be configured to be implanted in a blood vessel and can be expandable to an expanded state at the aneurysm. The flow-diverting device can comprise a frame and a mesh fixed to and extending across at least some of the frame. The flow-diverting device can be configured such that the mesh spans the neck of the aneurysm when the flow-diverting device is positioned in a blood vessel and adjacent to the aneurysm. The mesh can further have a porosity and/or pore size configured to interfere with blood flow to a degree sufficient to lead to thrombosis and healing of the aneurysm.

An aspect of at least some of the embodiments disclosed herein involves an expandable structure formed of a plurality of interconnected frame struts forming a plurality of frame cells and a plurality of interconnected mesh struts forming a plurality of mesh cells. The mesh struts can be configured to be flexible so that any tendency of the mesh to inhibit or affect the mechanical performance of the frame, or for the frame to tear or distort the mesh, can be reduced or eliminated. The flow-diverting device can therefore exhibit a high degree of flexibility such that when the device is placed along a sharp turn in a tubular structure, the shape of the device conforms to the turn radius at the sharp turn while remaining in apposition with the inner walls of the tubular structure.

The subject technology is illustrated, for example, according to various aspects described below. Various examples of aspects of the subject technology are described as numbered clauses (1, 2, 3, etc.) for convenience. These are provided as examples and do not limit the subject technology.

Clause 1. An expandable device comprising:
a frame comprising a plurality of interconnected frame struts forming frame cells; and
a flow-diverting mesh extending over at least a portion of a length and circumference of the frame and comprising a plurality of interconnected mesh struts forming mesh cells, wherein a thickness of the frame struts is greater than a thickness of the mesh struts.

Clause 2. The expandable device of clause 1, wherein the flow-diverting mesh is disposed on a radially outer side of the frame when the expandable device is in a tubular shape.

Clause 3. The expandable device of clause 1, wherein each of the mesh struts comprise connector struts extending circumferentially about the expandable device and bridge members connecting a series of connector struts.

Clause 4. The expandable device of clause 1, wherein, within each frame cell, between 10 and 100 mesh cells are formed.

Clause 5. The expandable device of clause 1, wherein the frame cells comprise at least two different shapes and/or sizes.

Clause 6. The expandable device of clause 1, wherein the mesh cells comprise at least two different shapes and/or sizes.

Clause 7. The expandable device of clause 1, wherein a shape of some or all of the frame cells is the same as a shape of some or all of the mesh cells.

Clause 8. The expandable device of clause 1, further comprising a proximal portion that tapers to a connection mechanism.

Clause 9. The expandable device of clause 8, wherein the flow-diverting mesh does not extend over any of the proximal portion.

Clause 10. The expandable device of clause 1, wherein the thickness and/or a width of the mesh struts is equal to or less than 10 µm.

Clause 11. The expandable device of clause 1, wherein the thickness and/or a width of the frame struts is equal to or less than 45 µm.

Clause 12. The expandable device of clause 1, wherein the flow-diverting mesh extends over a flow diverting portion of the frame, and the flow-diverting mesh does not extend over a portion of the frame that includes some of the frame cells and is disposed proximal to the flow diverting portion and/or a portion of the frame that includes some of the frame cells and is disposed distal to the flow diverting portion.

Clause 13. The expandable device of clause 1, wherein, a porosity provided by the flow diverting mesh is lower than a porosity provided by the frame.

Clause 14. A medical device comprising:
a frame including a plurality of interconnected frame struts, a plurality of first frame cells, and a plurality of second frame cells, wherein the plurality of first and second frame cells are formed between adjacent ones of the interconnected frame struts; and
a mesh including a plurality of interconnected mesh struts forming a plurality of mesh cells therebetween, wherein—
the mesh is fixed relative to the frame,
the mesh extends across the first frame cells,
the mesh cells have an area that is less than an area of the frame cells, and
the mesh is configured to divert the flow of a liquid.

Clause 15. The medical device of clause 14 wherein the frame struts and the mesh struts are configured to lengthen and/or shorten in response to external forces applied to the device.

Clause 16. The medical device of clause 14 wherein the plurality of mesh struts comprises a plurality of first mesh struts and a plurality of second mesh struts, and wherein individual first mesh struts extend across a corresponding one of the first frame cells and are connected to the frame at a perimeter of the corresponding first frame cell.

Clause 17. The medical device of clause 16 wherein the frame has a circumference, and wherein the plurality of first mesh struts extend circumferentially about the frame.

Clause 18. The medical device of clause 16 wherein individual second mesh struts connect to adjacent ones of the first mesh struts.

Clause 19. The medical device of clause 18 wherein the second mesh struts have a generally S-like shape and extend longitudinally farther than they extend circumferentially.

Clause 20. The medical device of clause 18 wherein—
in a first state, the second mesh struts extend longitudinally farther than they extend circumferentially, and
in a second state, the second mesh struts extend longitudinally to a lesser degree and circumferentially to a greater degree than in the first state.

Clause 21. The medical device of clause 14 wherein the frame includes a proximal portion and a distal portion, wherein the proximal portion includes only second frame cells, and wherein the mesh does not extend across the second frame cells.

Clause 22. The medical device of clause 14 wherein—
the frame includes a proximal portion, a distal portion, and a flow-diverting portion between the distal and proximal portions,
the flow-diverting portion includes only first frame cells,
the proximal and distal portions include only second frame cells, and
the mesh does not extend across the second frame cells.

Clause 23. The medical device of clause 14 wherein between 10 and 100 mesh cells are formed within each first frame cell.

Clause 24. The medical device of clause 14 wherein the first and second frame cells comprise at least two different shapes and/or sizes.

Clause 25. The medical device of clause 14 wherein the mesh cells comprise at least two different shapes and/or sizes.

Clause 26. The medical device of clause 14 wherein a thickness and/or a width of the mesh struts is equal to or less than 10 µm, and wherein a thickness and/or a width of the frame struts is equal to or less than 45 µm.

Clause 27. The medical device of clause 14 wherein a shape of some or all of the first frame cells is the same as a shape of some or all of the mesh cells.

Clause 28. A device for diverting blood flow in a vessel, comprising:
a plurality of interconnected frame struts defining a plurality of first cells therebetween, the first cells having a perimeter;
a plurality of connector struts extending across at least some of the first cells, wherein individual connector struts are connected to the perimeter of a corresponding one of the first cells and have a thickness that is less than a thickness of the frame struts;
a plurality of bridge struts connected to at least adjacent ones of the connector struts, wherein the bridge struts have a thickness that is less than the thickness of the frame struts; and
a plurality of second cells formed by the connector struts and the bridge struts, wherein the second cells have an area that is less than an area of the first cells, and wherein the second cells are configured to divert blood flow.

Clause 29. The device of clause 28 wherein the frame struts have a generally sinusoidal-like shape, wherein the bridge struts have a generally S-like shape, and wherein the bridge struts and frame struts are configured to lengthen or shorten in response to external forces applied to the device.

Clause 30. The device of clause 28 wherein the device has a circumference, wherein the connector struts have a periodic shape and extend circumferentially, and wherein the connector struts are configured to lengthen or shorten in response to external forces applied to the device.

Clause 31. An expandable device for diverting blood flow in a vessel lumen, the device comprising:
a proximal portion including a plurality of first cells;
a distal portion having a generally tube-like shape in an expanded state and including a plurality of second cells; and
a mesh including a plurality of pores and extending across at least some of the second cells in the distal portion, wherein— the mesh is fixed relative to the second cells,
a porosity of the mesh is less than a porosity of the distal portion and less than a porosity of the proximal portion, and
the mesh is configured to divert blood from flowing through the second cells.

Clause 32. The medical device of clause 31 wherein the mesh is attached to a radially outer side of the distal portion of the device.

Clause 33. The medical device of clause 31 wherein the proximal portion tapers to a connector configured to be removably coupled to a delivery wire.

Additional features and advantages of the present technology will be set forth in the description below, and in part will be apparent from the description, or may be learned by practice of the present technology. The advantages of the present technology will be realized and attained by the structure particularly pointed out in the written description and clauses hereof as well as the appended drawings.

It is to be understood that both the foregoing general description and the following detailed description are exemplary and explanatory and are intended to provide further explanation of the present technology.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 2A is a plan view of another embodiment of a flow-diverting device configured in accordance with the present technology.

FIG. 2B is an enlarged plan view of a portion of the device shown in FIG. 2A.

FIG. 3A is a plan view of another embodiment of a flow-diverting device configured in accordance with the present technology.

FIG. 3B is an enlarged plan view of a portion of the device shown in FIG. 3A.

DETAILED DESCRIPTION

In the following detailed description, specific details are set forth to provide an understanding of the present technology. However, the present technology may be practiced without some of these specific details. In some instances, well-known structures and techniques have not been shown in detail so as not to obscure the present technology.

The terminology used in the description presented below is intended to be interpreted in its broadest reasonable manner, even though it is being used in conjunction with a detailed description of certain specific embodiments of the disclosure. Certain terms may even be emphasized below; however, any terminology intended to be interpreted in any restricted manner will be overtly and specifically defined as such in this Detailed Description section.

Aspects of the present disclosure are directed generally toward devices that can be delivered into a vascular system to divert flow. According to some embodiments, such devices are provided for treating aneurysms by diverting flow. For example, a device according to the present technology can be configured to interfere with blood flow to generally reduce the exchange of blood between a parent vessel and an aneurysm, which can induce thrombosis of the aneurysm. A device (or a device component, such as a frame and/or mesh) that interferes with blood flow can be said to have a "flow diverting" property.

Figure 1A:
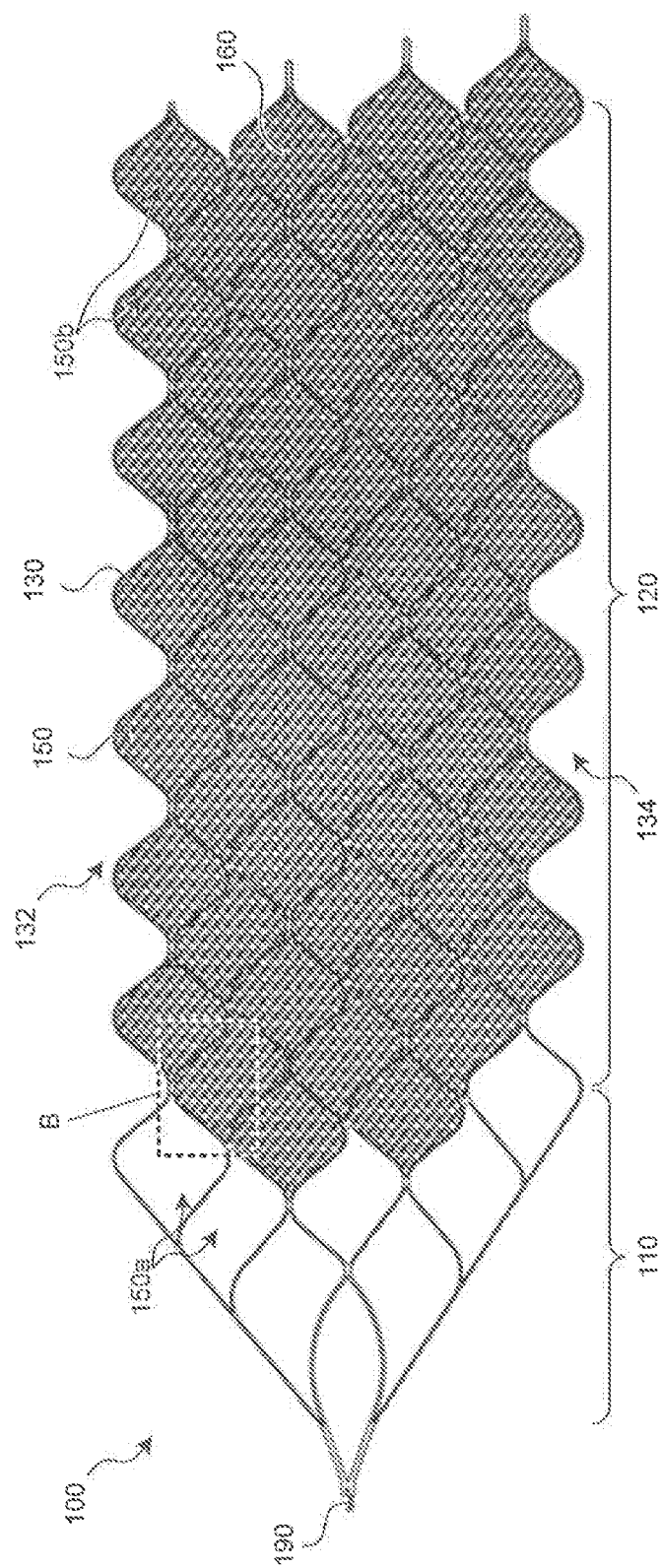
FIG. 1A is a plan view of a flow-diverting device configured in accordance with the present technology.
Figure 1B:
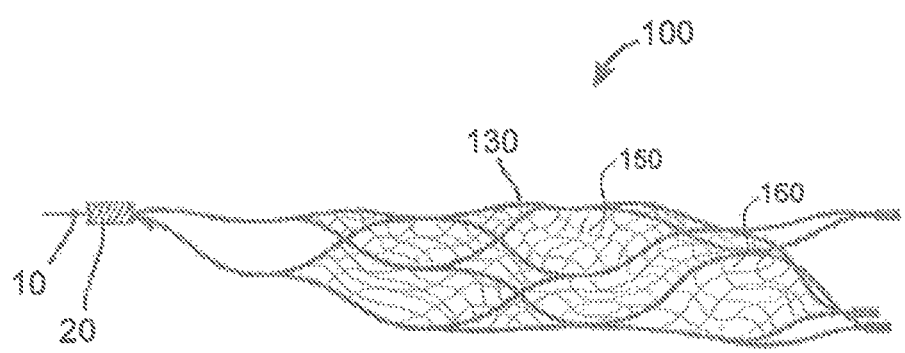
FIG. 1B is a schematic illustration of the device shown in FIG. 1A, showing the device in a tubular configuration.

FIG. 1A is a plan view of an expandable flow-diverting device 100 ("device 100") in an uncurled or laid-flat configuration. As shown in FIG. 1A, the device 100 includes a frame 130 forming a plurality of frame cells 150, and a flow-diverting mesh 160 ("mesh 160") extending across at least some of the frame cells 150. The frame 130 includes longitudinal edges 132 and 134. FIG. 1B is a schematic illustration of the device 100 of FIG. 1A showing the device 100 in a tubular configuration and coupled to a delivery wire 10 via connector 20. As demonstrated by FIGS. 1A and 1B, the frame 130 may be configured to curl up from the laid-flat configuration (FIG. 1A) into the tubular configuration (FIG. 1B) such that longitudinal edges 132 and 134 (not shown in FIG. 1B) are positioned adjacent to or in contact with one another and the frame 130 surrounds a lumen extending between open ends of the device 100. In some embodiments, the longitudinal edges 132 and 134 may overlap when the device 100 is in the tubular configuration. While the views provided in several of the figures provided herein show expandable devices laid flat for ease of explanation and understanding, the devices can be formed into a tubular shape. Also, as used herein, the term "longitudinal" can refer to a direction along an axis that extends through the lumen of the device while in a tubular configuration, and the term "circumferential" can refer to a direction along an axis that is orthogonal to the longitudinal axis and extends around the circumference of the device when in a tubular configuration.

In the embodiment shown in FIG. 1A, the mesh 160 extends across all of the frame cells 150 in a distal portion 120 of the device 100, and is not disposed on or across any of the frame cells 150 in a proximal portion 110 of the device 100. The proximal portion 110 may include one or more tapered sections with frame cells 150 that have a different size than the individual frame cells 150 of the distal portion 120. For example, as illustrated in FIG. 1A, individual frame cells 150a in the proximal portion 110 can have a longitudinal length that is longer than individual frame cells 150b in the distal portion 120. Accordingly, the frame cells 150 can comprise at least two different shapes and/or sizes. In some embodiments, the distal portion 120 and/or proximal portion 110 can each include frame cells 150 having at least two different shapes and/or sizes.

The proximal portion 110 may taper gradually towards a connector 190, or some other connection point along the device 100 that connects the device 100 to a delivery wire (e.g., as shown in FIG. 1B). The connector 190 permits the device 100 to be released from the delivery wire within a vessel. In some embodiments, the connector 190 may include an electrolytically severable region that corrodes or dissolves under the influence of electrical energy when in contact with an electrolyte. Where an electrolytically severable connection is employed, the device 100 may be isolated from electric current such that during detachment of the device 100, only the electrolytically severable region of the connector 190 disintegrates in blood, and the device 100 separates from the delivery wire cleanly at the electrolytically severable region. In other embodiments, the connector 190 can comprise another type of releasable mechanism such as a mechanically releasable connection. In yet other embodiments, the connector 190 can comprise a thermally or electrothermally releasable connection that functions by heating and melting a connection area.

The device 100 is configured to be self-expanding to a relaxed state or an expanded state from a compressed state. As used herein, the relaxed state is one to which the device 100 will self-expand in the absence of any containment or external forces. The device 100 can have a maximum diameter in the relaxed state. As used herein, the expanded state is one to which the device 100 is capable of self-expanding in a contained environment, such as within a blood vessel. For example and simplicity of measurement, this expanded state can be one to which the device 100 will self-expand within a straight, non-tapering cylindrical tube with an inside diameter that is slightly smaller than the maximum diameter of the device 100 in the relaxed state. As used herein, the compressed state is the state of the device 100 when in a more contained environment than the expanded state, such as within a catheter. For example and simplicity of measurement, this compressed state can be the state of the device when it is within a straight, non-tapering cylindrical tube with an inside diameter that is significantly smaller than the maximum diameter of the device 100 in the relaxed state.

The device 100 further includes a first longitudinal edge 132 and a second longitudinal edge 134. The first longitudinal edge 132 and the second longitudinal edge 134 may be connected to each other to form a circumferentially continuous shape by welding, soldering, or otherwise joining the first and second longitudinal edges 132 and 134. For example, the first and second longitudinal edges 132 and 134 can be connected to each other so that the distal portion 120 of the device 100 has a generally tube-like or substantially cylindrical shape. In other embodiments, the device 100 is not circumferentially continuous. For example, the first longitudinal edge 132 and the second longitudinal edge 134 may be formed by cutting a preformed, etched, or laser-cut tube longitudinally along the length of the tube. Regardless of the manner of forming, the device 100 may be rolled or curled such that the first and second longitudinal edges 132 and 134 overlap one another when the device 100 is in the compressed state and/or the expanded state. Upon release from the compressed state (e.g., from within a catheter), the device 100 (when configured to be self-expanding) may spring open and attempt to assume the expanded state.

Figure 1C:
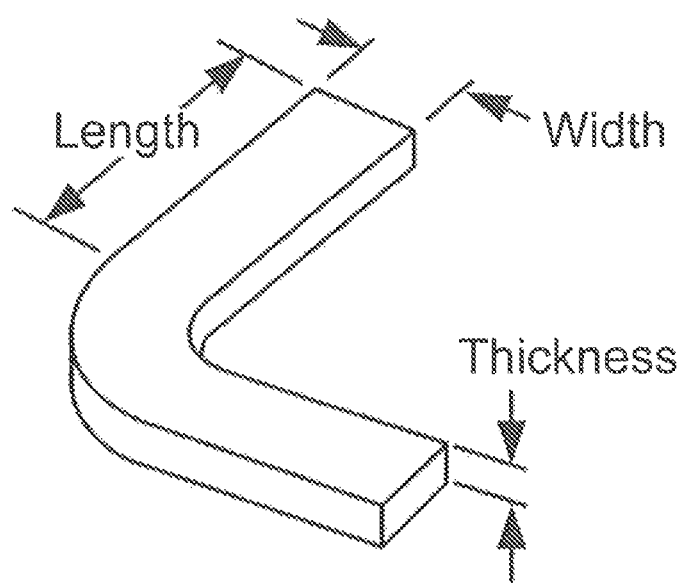
FIGS. 1C and 1D are a perspective view and a cross-sectional view, respectively, of a strut of a flow-diverting device configured in accordance with the present technology.
Figure 1D:
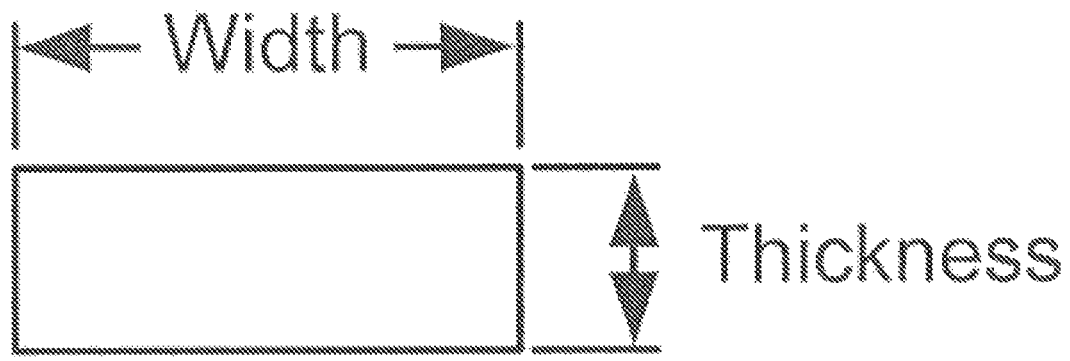

As described in further detail below, the mesh 160 and frame 130 can each comprise a plurality of interconnected struts. FIG. 1C depicts a perspective view, and FIG. 1D depicts a cross-sectional view, of a strut according to some embodiments of the present technology. As shown, the strut has a length, a width, and a thickness. The thickness can be measured as a dimension that is orthogonal to a central axis when the device 100 is considered in a tubular shape, or as a dimension that is orthogonal to a plane of the device 100 when represented as laid-flat. The length can be measured as a distance extending between ends of a strut, where the ends connect to another structure. The width can be measured as the distance that is generally orthogonal to the length and thickness. The width and length of a strut can contribute to a surface coverage and porosity of the device 100. According to some embodiments, the strut can have a square cross-section. However, the strut may have other suitable cross-sectional shapes, such as rectangular, polygonal, round, ovoid, elliptical, or combinations thereof.

Figure 1E:
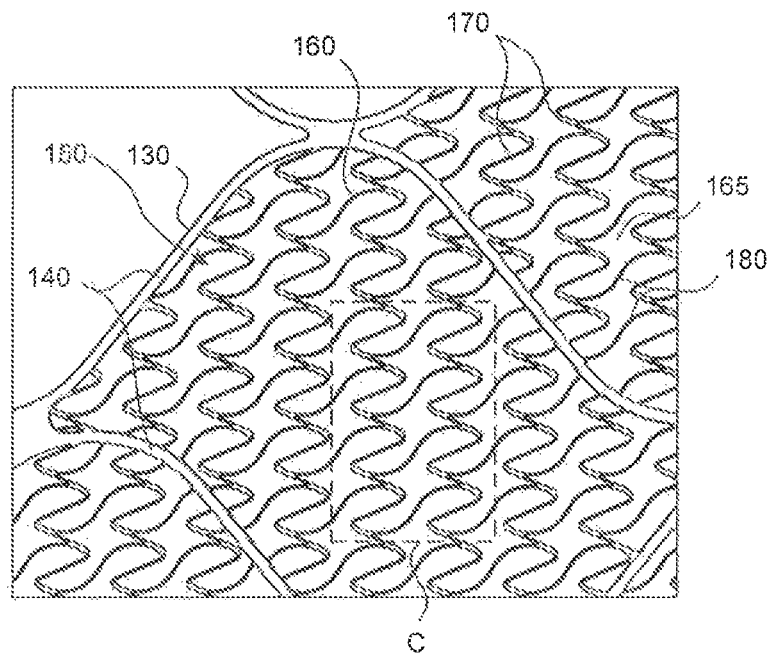
FIG. 1E is an enlarged plan view of a portion of the device shown in FIG. 1A.

FIG. 1E is an enlarged plan view of a portion (illustrated by the dashed box B in FIG. 1A) of the device 100 shown in FIG. 1A. As depicted in FIG. 1E, the mesh 160 extends across only some of the frame cells 150 of the frame 130. The mesh 160 is fixed relative to the frame 130. For example, the mesh 160 can be bonded or coupled to the frame 130, or the mesh 160 can be formed monolithically with the frame 130. In some embodiments, the mesh 160 is disposed on a radially outer side of the frame 130, such that the mesh 160 is placed against a body vessel when the device 100 is in the expanded state within the body vessel. In other embodiments, the mesh 160 is disposed on a radially inner side of the frame 130. In yet other embodiments, the mesh 160 is level with or within individual frame cells 150 of the frame 130.

The frame 130 includes a plurality of interconnected frame struts 140 forming the frame cells 150 therebetween. As illustrated in FIGS. 1A and 1E, frame cells 150 are defined between adjacent ones of the frame struts 140. The frame struts 140 can have an undulated shape (e.g., sinusoidal or S-like) and can extend longitudinally across some or all of the distal portion 120 of the device 100. The frame struts 140 can be connected to each other at or near peaks or troughs of their undulated shape. In other embodiments, the frame struts 140 can have any other suitable shape or configuration. The thickness and/or width of the frame struts 140 can be equal to or less than 45 μm. For example, the thickness and/or width of the frame struts 140 can be 20 to 45 μm.

The frame struts 140 are configured to facilitate expansion, contraction, elongation, foreshortening, distortion, etc. of the frame 130 as the device 100 is expanded, contracted, bent, etc. during delivery and deployment. For example, in embodiments where the frame struts 140 have a generally S-like shape, the frame struts 140 can stretch out (e.g., a distance between peaks and troughs of the frame struts 140 can increase) when the device 100 is elongated. Conversely, the frame struts 140 can compress (e.g., the distance between the peaks and troughs of the frame struts 140 can decrease) when the device 100 is foreshortened. As the frame struts 140 change in shape during delivery and deployment, the frame cells 150 correspondingly change in shape. For example, as the frame struts 140 that form an individual frame cell 150 are stretched, a longitudinal length of the frame cell 150 can increase while a circumferential height decreases. Likewise, as the frame struts 140 that form an individual frame cell 150 are compressed, a circumferential height of the frame cell 150 can increase while a longitudinal length decreases. Accordingly, the frame struts 140 are configured such that the frame 130 is flexible. This permits the device 100 to be snuggly placed within tortuous regions of the vasculature (e.g., in vessels that are curved, twisted, forked, etc.).

The mesh 160 includes a plurality of interconnected mesh struts (e.g., identified individually as connector struts 170 and bridge struts 180) forming mesh cells 165. The mesh struts 170 and 180 are fixed relative to the frame struts 140 and can be connected to the frame 130 along some or all of the perimeter of an individual frame cell 150 (or of some or all frame cells 150). For example, the mesh struts 170 and 180 can be secured to or monolithically formed with the frame struts 140. In certain embodiments, the number of mesh cells 165 is greater than a number of frame cells 150. The number of mesh cells 165 can be 10 to 200 times greater than the number of frame cells 150. For example, within each frame cell 150, between 10 and 200 mesh cells 165 can be formed. While the flow-diverting mesh 160 can extend over or under the frame 130, a mesh cell 165 is considered to be within a frame cell 150 if any portion of the mesh cell 165 extends over or across any portion of the frame cell 150.

A porosity of the device 100 can be defined as a ratio of an open surface area of the device 100 to a total surface area of the device 100. Accordingly, the mesh 160 provides a porosity that is lower than a porosity provided by the frame 130 alone. For example, the porosity provided by the mesh 160 can be in the range of 5%-95%. The mesh cells 165 can provide a pore size that is smaller than a pore size provided by the frame cells 150. That is, the mesh cells 165 enclose an area that is less than the frame cells 150 (e.g., as measured via a maximum-inscribed-circle technique). The pore size provided by the mesh cells 165 can be between 2 μm and 35 μm.

The mesh 160 can comprise the primary flow diverting section of the device 100. When the device 100 is positioned with a body vessel, the mesh 160 can provide embolic properties that interfere with blood flow in or into the body space (e.g., an aneurysm) in or across which the device 100 is deployed. Specifically, the porosity and/or pore size of the mesh 160 of the device 100 can be configured to, for example, interfere with blood flow to a degree sufficient to lead to thrombosis of the aneurysm or other body space.

As shown in FIG. 1E, the mesh 160 includes a plurality of connector struts 170 extending across individual frame cells 150. The connector struts 170 can be connected to the frame 130 at one or more positions along the perimeter of an individual frame cell 150. As shown in the embodiment of FIG. 1E, opposing longitudinal ends of the connector struts 170 can be connected to adjacent frame struts 140 that form the corresponding frame cell 150. In some embodiments, the connector struts 170 can further be connected to other connector struts 170 to form bands or columns that extend along some or all of a circumference of the device 100 when the device 100 forms a tubular shape. The connector struts 170 can have a periodic, undulated, and/or "zigzag" shape. In certain embodiments, the connector struts 170 have the same or a generally similar shape as the frame struts 140. The thickness and/or width of the connector struts 170 can be equal to or less than 10 μm, for example 5 μm. In some embodiments, the connector struts 170 can alternate in width along their length. For example, FIG. 1E illustrates connector struts 170 that alternate between relatively wide and relatively narrow along their length.

In the embodiment illustrated in FIGS. 1A and 1E, the mesh 160 further comprises a plurality of bridge struts 180. One or more bridge struts 180 can connect adjacent ones of the connector struts 170. For example, opposing longitudinal ends of the bridge struts 180 can be connected to adjacent connector struts 170. Similarly, one or more bridge struts 180 can connect adjacent ones of the frame struts 140 and/or connect individual connector struts 170 to a corresponding bridge strut 140. The connector struts 170 and bridge struts 180 together form the plurality of mesh cells 165. The shape of the mesh cells 165 depends on the shape and configuration of the connector struts 170 and bridge struts 180. The thickness and/or width of the bridge struts 180 can be equal to or less than 10 μm, for example 5 μm. In other embodiments, the mesh 160 does not include bridge struts 180 and only comprises the connector struts 170.

The bridge struts 180 generally extend longitudinally along the device 100 between adjacent connector struts 170 and have a shape including two curved sections (e.g., forming an S-like shape). In other embodiments, the bridge struts 180 can have other suitable shapes (e.g., sinusoidal, periodic, linear, z-shaped, etc.). FIG. 1E illustrates the mesh 160 in a state in which the bridge struts 180 extend circumferentially to a lesser degree than they do longitudinally (e.g., the bridge struts extend longitudinally further than they extend circumferentially). In other states, the bridge struts 180 can extend circumferentially more or equally to the degree they extend longitudinally. As explained in more detail below, the bridge struts 180 are flexible to permit elongation and foreshortening of the mesh 160, as necessary, during compression, expansion, or bending of the device 100 that occurs during delivery and deployment.

Figure 1F:
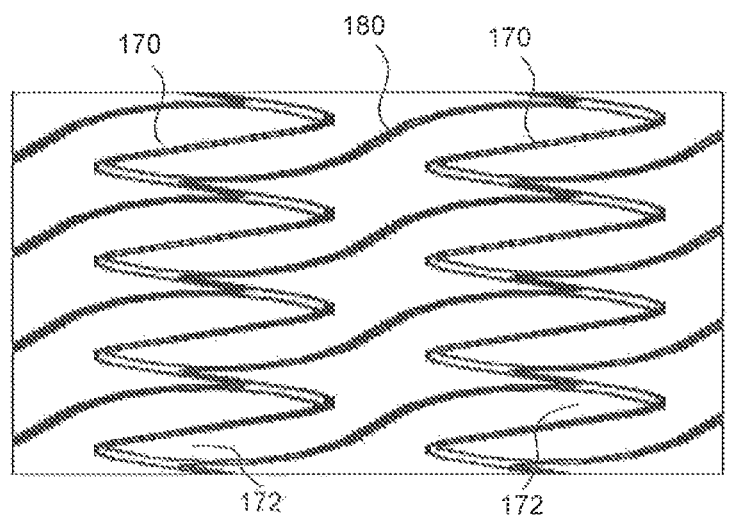
FIG. 1F is an enlarged plan view of a portion of the device shown in FIGS. 1A and 1E, showing the device in a different state.

FIG. 1F is an enlarged plan view of a portion (illustrated by the dashed box C) of the device 100 shown in FIG. 1E, and showing the mesh 160 in a different, more elongated state than illustrated in FIG. 1E. Such a state may occur when the device 100 is delivered or deployed into tortuous regions of the vasculature. As shown, the bridge struts 180 extend longitudinally to a greater degree and extend circumferentially to a lesser degree than in the state illustrated in FIG. 1E. Moreover, the bridge struts 180 can have a more elongated S-like shape in which the curved sections are relatively more flattened. At the same time, the connector struts 170 can have a more compressed shape in which the distance between peaks and/or troughs (e.g., troughs 172) of the undulated connector struts 170 are closer together than in the state illustrated in FIG. 1E.

Conversely, the mesh 160 is also configured to accommodate foreshortening of the device 100. For example, in contrast to the state shown in FIG. 1F, the bridge struts 180 can extend circumferentially to a greater degree and extend longitudinally to a lesser degree to accommodate foreshortening of the device 100. Likewise, the connector struts 170 can take on a more expanded shape as, for example, the distance between troughs 172 increases. As the shape of the connector struts 170 and bridge struts 180 change, the shape of the mesh cells 165 correspondingly change. For example, when the mesh 160 is in an elongated state such as that shown in FIG. 1F, the mesh cells 165 can have a longitudinal length that is greater, and a circumferential height that is less, than in the state shown in FIG. 1E or a foreshortened state.

Moreover, in certain embodiments, instead of or in addition to employing an S-like shape for the bridge struts 180, one or both ends of the bridge struts 180 can connect to the trough of an adjacent connector strut 170. For example, as depicted in FIG. 1F, the individual bridge struts 180 are connected to corresponding troughs 172 of the individual connector struts 170. The bridge struts 180 can therefore be made longer—and accordingly better able to elongate or foreshorten—without requiring an increase in the distance between adjacent connector struts 170. This permits the mesh 160 to retain a low porosity while also being made more flexible.

Accordingly, the mesh 160 is configured to be flexible and to accommodate compression, expansion, elongation, foreshortening, and/or bending of the device 100 during delivery and deployment. As described above, the frame 130 is also configured to be flexible so that the device 100 can be snuggly placed within tortuous regions of the vasculature (e.g., in vessels that are curved, twisted, forked, etc.). The mesh 160 and frame 130 are therefore independently flexible while still being immovably attached to each other. Importantly, because the mesh 160 can accommodate elongation, foreshortening, etc., in the manner described above, any tendency of the mesh 160 to inhibit or affect the mechanical performance of the frame 130, or for the frame 130 to tear or distort the mesh 160, can be reduced or eliminated. The device 100 can therefore exhibit a high degree of flexibility that allows it to be placed in tortuous regions of the vasculature, while also including a flow-diverting mesh 160 that retains a sufficiently small pore size to treat aneurysms therein.

Moreover, the flexibility of the device 100 can facilitate accurate placement of the device 100 within the vasculature—compared to other commercially available devices, including braided devices. In certain embodiments, some or all of the frame struts 140 can comprise a radiopaque marker. The radiopaque marker can be disposed on a substantially straight section of a frame strut 140 so that the radiopaque marker is predominantly not subject to bending or flexing. The radiopaque marker can extend from a frame strut 140 into a frame cell 150 and/or a mesh cell 165. One or more mesh struts 170 or 180 can be omitted from a pattern to accommodate the presence of the radiopaque marker. The radiopaque marker can be formed on the frame struts 140 by a process that is the same or different than a process used to form the frame 130 and/or the mesh 160, as discussed further herein.

The device 100 can be advantageously placed in a body vessel to treat an aneurysm therein. For example, the device 100 can be positioned so that the mesh 160 is placed across the neck of the aneurysm to impede blood flow along an aneurysmal flow path between the prevailing direction of arterial flow and the interior of the aneurysm. The device 100 can therefore facilitate endothelial growth across the neck of the aneurysm or otherwise across the aneurysmal flow path. Moreover, the device 100 can have a thickness that is small enough to enable placement in smaller blood vessels, thereby opening new areas of treatment for flow diversion.

According to some embodiments, struts of a flow-diverting mesh can form a pattern other than that shown in FIGS. 1A, 1D, and 1E. The shape and size of mesh cells can be altered while still providing a flow-diverting function when placed over an opening in a body vessel, such as an ostium of an aneurysm. For example as shown in FIG. 2A, a device 200 may include a proximal portion 210 and a distal portion 220. The proximal portion 210 may taper gradually towards a connector 290. The device 200 can further comprise a frame 230 including a plurality of interconnected frame struts 240 forming frame cells 250 between the frame struts 240. A mesh 260 can extend across a portion of the frame cells 250. Features of the device 200 that are identified with reference numerals that differ from the reference numerals for the device 100 by a multiple of 100 can have the same aspects as the corresponding features in the device 100, unless noted otherwise.

FIG. 2B is an enlarged plan view of a portion of the device 200 shown in FIG. 2A. As illustrated in FIG. 2B, the mesh 260 can comprise a plurality of interconnected mesh struts (e.g., connector struts 270 and bridge struts 280) forming mesh cells 265. Opposing longitudinal ends of the connector struts 270 can be connected to the perimeter of an individual frame cell 250. For example, as shown in FIG. 2B, individual connector struts 270 can be connected to adjacent frame struts 240 that form a corresponding frame cell 250. In some embodiments, the connector struts 270 can further be connected to other connector struts 270 to form bands or columns that extend along some or all of a circumference of the device 200 when the device 200 forms a tubular shape. The connector struts 270 can have a saw-tooth-like shape and can be interconnected at a plurality of vertices 276. A plurality of mesh cells 265a formed between connector struts 270 can have a generally diamond-like shape, thereby forming bands or columns of diamond-shaped mesh cells 265a.

The mesh 260 further comprises a plurality of bridge struts 280. One or more bridge struts 280 can connect adjacent ones of the connector struts 270. For example, opposing longitudinal ends of the bridge struts 280 can be connected to adjacent connector struts 270. The bridge struts 280 and connector struts 270 can combine to form a plurality of mesh cells 265b that have a different shape from the mesh cells 265a. For example, the mesh cells 265b can have a generally hourglass-like or other shape.

As depicted in FIG. 2B, the bridge struts 280 can extend longitudinally along the device 200 between adjacent connector struts 270 and have a shape including two curved sections (e.g., forming an S-like shape). The bridge struts 280 can extend circumferentially to a lesser or greater degree than they do longitudinally to facilitate elongation and foreshortening of the bridge struts 280, as necessary, during compression, expansion, bending, etc., of the device 200. In some embodiments, the connector struts 270 can have a more compressed shape (e.g., forming diamond-shaped mesh cells 265 with a greater longitudinal length than circumferential height) than the embodiment illustrated in FIG. 2B, when the device 200 is compressed, expanded, or bent. Thus the mesh 260 can accommodate compression, expansion, bending, etc. of the device 200 during delivery and deployment. Because the mesh 260 can accommodate elongation, foreshortening, etc. in the manner described above, any tendency of the mesh 260 to inhibit or affect the mechanical performance of the frame 230, or for the frame 230 to tear or distort the mesh 260, can be advantageously reduced or eliminated. The device 200 can therefore exhibit a high degree of flexibility that allows it to be placed in tortuous regions of the vasculature, while also including a flow-diverting mesh 260 that retains a sufficiently small pore size to treat aneurysms therein.

Instead of or in addition to such an S-shaped bridge strut 280, one or both ends of the bridge struts 280 can connect to an adjacent connector strut 270 at or near a vertex 276 of the connector struts 270. For example, FIG. 2B illustrates an embodiment in which the bridge struts 280 are connected to the vertices 276 of the connector struts 270. The bridge struts 280 can therefore be made longer—and accordingly better able to elongate or foreshorten—without the need to increase the distance between adjacent connector struts 270.

According to some embodiments, struts of a flow-diverting mesh can form a pattern that is similar to the pattern of struts that form a frame. The shape of frame cells and mesh cells can be the same or similar, while the size of the mesh cells are substantially smaller than that of the frame cells. For example, FIG. 3A shows a device 300 including a frame 330 and a flow-diverting mesh 360 having a similar pattern, but made on a smaller scale. The device 300 includes a proximal portion 310 and a distal portion 320. The proximal portion 310 may taper gradually towards a connector 390. The frame 330 includes a plurality of interconnected frame struts 340 forming frame cells 350 between the frame struts 340. The frame struts 340 can have an undulated shape (e.g., sinusoidal or comprising S-curves) and can extend longitudinally across some or all of the distal portion 320 of the device 300. The mesh 360 can extend across a portion of the frame cells 350. Features of the device 300 that are identified with reference numerals that differ from the reference numerals for the device 100 by a multiple of 100 can have the same aspects as the corresponding features in the device 100, unless noted otherwise.

FIG. 3B is an enlarged plan view of a portion of the device 300 shown in FIG. 3A. As illustrated in FIG. 3B, the mesh 360 can comprise a plurality of interconnected mesh struts 370 forming mesh cells 365 therebetween. The mesh struts 370 can have an undulated shape (e.g., sinusoidal or comprising S-curves). Individual mesh struts 370 extend longitudinally across a corresponding frame cell 350 and are connected to the perimeter of the corresponding frame cell 350. The mesh struts 370 can be connected to each other at or near peaks or troughs thereof. In the embodiment illustrated in FIGS. 3A and 3B, the mesh 360 does not include bridge struts. In some embodiments, the mesh may include a plurality of bridge struts extending between and connecting the mesh struts 370. In certain embodiments, bridge struts can extend circumferentially to a greater degree than they extend longitudinally to connect adjacent mesh struts 370.

In some embodiments, at least a portion of the mesh 360 can have the same shape as the frame 330. For example, the mesh struts 370 and the mesh cells 365 can have the same shape as the frame struts 340 and the frame cells 350, respectively. However, the mesh struts 370 and the mesh cells 365 can have a size that is different than that of the frame struts 340 and the frame cells 350, respectively. Accordingly, the pattern of the mesh 360 can be a small-scaled pattern of the frame 330. In some embodiments, the mesh 360 is bonded to, coupled to, or formed monolithically with the frame 330 in such a manner that the mesh struts 370 are fixed relative to (or secured to) the frame struts 340 along some or all of the perimeter of an individual frame cell 350 (or of some or all frame cells 350). In such an embodiment, employing a pattern for the mesh 360 that is similar or identical to—but smaller in scale than—that employed for the frame 330 permits the mesh 360 to mimic the expansion, contraction, elongation, foreshortening, distortion, etc. of the frame cells 350 as the device 300 is expanded, contracted, bent, etc., during delivery and deployment. Thus, any tendency of the mesh 360 to inhibit or affect the mechanical performance of the frame 330, or for the frame 330 to tear or distort the mesh 360, can be reduced or eliminated. The device 300 can therefore exhibit a high degree of flexibility that allows it to be placed in tortuous regions of the vasculature, while also including a flow-diverting mesh 360 that retains a sufficiently small pore size to treat aneurysms therein.

Figure 4:
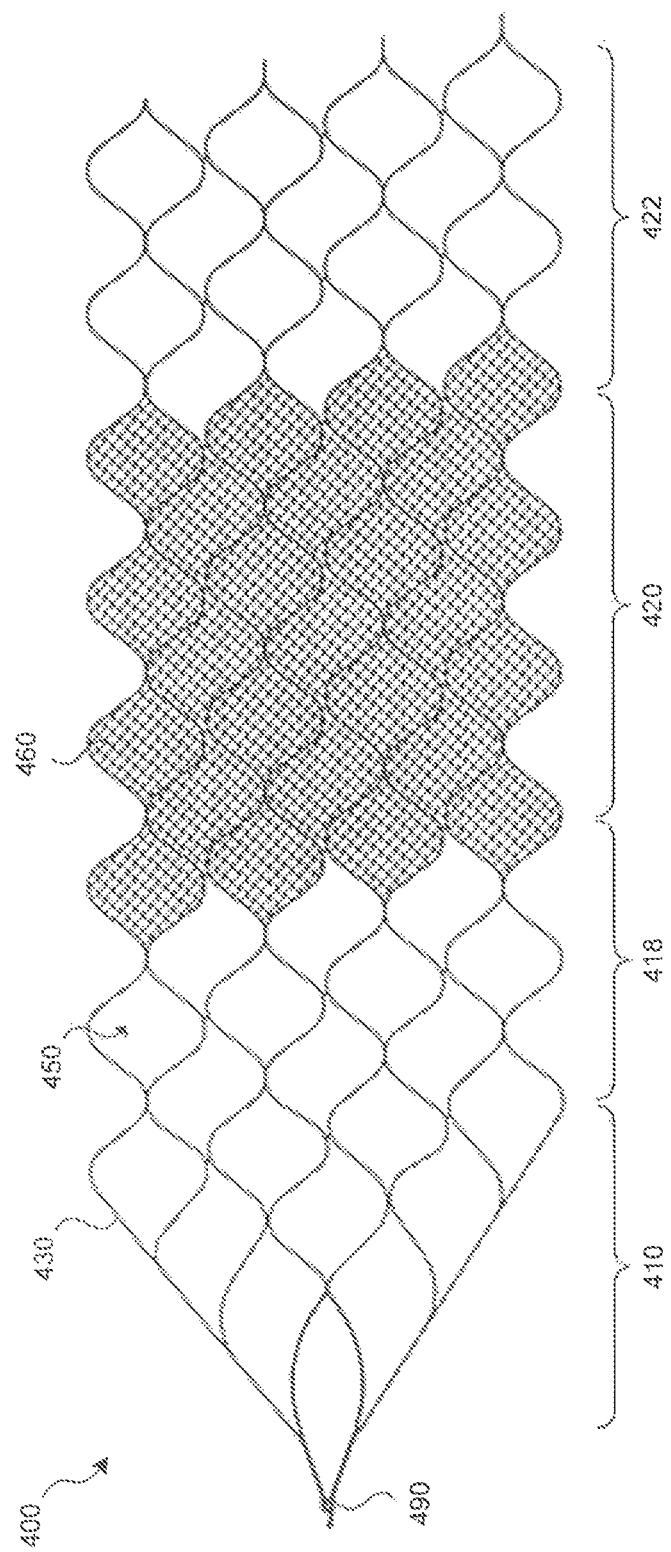
FIG. 4 is a plan view of yet another embodiment of a flow-diverting device configured in accordance with the present technology.

FIG. 4 illustrates another embodiment of a flow-diverting device configured in accordance with the present technology. The device 400 includes include a proximal portion 410, a first distal portion 418, a second distal portion 420 (e.g., a flow-diverting portion), and a third distal portion 422. The proximal portion 410 may taper gradually towards a connector 490. The device 400 can comprise a frame 430 and a mesh 460 extending across a portion of the frame 430. The frame 430 and mesh 460 can be configured as in any of the embodiments described above with reference to FIGS. 1E, 2B and 3B. Features of the device 400 that are identified with reference numerals that differ from the reference numerals for the device 100 by a multiple of 100 can have the same aspects as the corresponding features in the device 100, unless noted otherwise.

In the embodiment shown in FIG. 4, the mesh 460 can be confined to the second distal portion 420, such that the mesh 460 does not extend across any of the frame cells 450 in the first distal portion 418 or the third distal portion 422. The second distal portion 420 can be configured to overlie an aneurysm for flow diversion therapy, while the first distal portion 418 and/or the third distal portion 422 can overlie a branch vessel to simultaneously allow perfusion to the adjacent branch vessel whose ostium is crossed by a portion of the device 400. That is, the device 400 can be advantageously positioned to inhibit blood flow into an aneurysm while not also inhibiting flow to branching or secondary vessels that are close to the aneurysm.

A flow-diverting device configured in accordance with the present technology may be formed, for example, by laser cutting a pre-formed tube or sheet, by interconnecting components (e.g., by laser welding), by vapor deposition techniques, or by combinations thereof. A frame can be formed by the same process as a mesh, or the frame can be formed by a process different than that by which the mesh is formed. The device can be formed using known flexible materials such as nitinol, stainless steel, cobalt-chromium alloys, Elgiloy, magnesium alloys, tungsten, tantalum, platinum, or combinations thereof.

In certain embodiments, a flow-diverting device can be formed by a photolithography process. For example, a substrate can be provided with a base for supporting the formation of the device. The base (e.g., copper) can be used temporarily as a buffer between the substrate and a primary material used to form the frame. After the base is provided on the substrate, the primary material is provided thereon, for example by vapor deposition. The primary material can be provided as a thin film of substantially uniform thickness. The thickness of the primary material can correspond to the desired thickness of the frame, as described herein. Portions of the primary material can be removed to form the structure of the frame. For example, a photomask, based on a strut pattern, can be used to selectively expose portions of the primary material to light and etch the primary material into the desired shape for the frame. Alternatively or in combination, a chemical agent can be used to remove the portions of the primary material that are not protected by a photoresist.

After the primary material is formed into the frame, a secondary material used to form the mesh is provided thereon, for example by vapor deposition. The secondary material can be provided as a thin film of substantially uniform thickness. The thickness of the secondary material can correspond to the desired thickness of the mesh, as described herein. Portions of the secondary material can be removed to form the structure of the mesh, while preserving the structure of the frame. For example, a photomask, based on a strut pattern, can be used to selectively expose portions of the secondary material to light and etch the secondary material into the desired shape for the mesh. Alternatively or in combination, a chemical agent can be used to remove the portions of the secondary material that are not protected by a photoresist.

The base can then be eroded to separate the device (frame and mesh) from the substrate. The device can be further treated to form a desired shape (e.g., tubular) and have the desired heat set and/or shape memory properties.

In other embodiments, a flow-diverting device can be formed by a laser cutting process. The device may be formed by cutting a pattern of struts on a tube or on a flat sheet and then rolling the flat sheet into a generally tube-like or coiled shape. As described above, the device can be can be circumferentially continuous or discontinuous while in a generally tube-like or coiled shape. Where the device is circumferentially discontinuous, portions of the device can overlap in certain states.

In yet other embodiments, the frame can be formed by a laser cutting process, and the mesh can be formed on the frame by vapor deposition and photolithography, as described above.

The present technology also includes methods of treating a vascular condition, such as an aneurysm, with any of the embodiments of the flow-diverting devices disclosed herein. A flow-diverting device according to the present technology can be deployed across the neck of an aneurysm and its flow-diverting properties employed to reduce blood flow between the aneurysm and the parent vessel. By reducing the blood flow to the aneurysm, the blood inside the aneurysm can be caused to thrombose, and to thereby lead to healing of the aneurysm.

In order to implant any of the flow-diverting devices disclosed herein, the device can be mounted in a delivery system. Generally, the delivery system can include an elongate delivery wire that supports or contains the device, and both components can be slidably received in a lumen of a microcatheter or other elongate sheath for delivery to any region to which the distal opening of the microcatheter can be advanced. The delivery wire is employed to advance the device through the microcatheter and out the distal end of the microcatheter so that the device is allowed to self-expand into place in the blood vessel, across an aneurysm or other treatment location. Accordingly, a vascular treatment apparatus can comprise a delivery system and a flow-diverting device, such as any of the devices described herein, mounted in or supported by the delivery system.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery or coronary artery. (As configured for neurovascular use, any of the devices disclosed herein can have a diameter of 2-8 mm in the relaxed state or the expanded state; devices used in the peripheral or coronary vasculature can have a diameter of 1-20 mm in the relaxed state or the expanded state.) The microcatheter is then advanced over the guidewire to the treatment location and situated so that a distal open end of the microcatheter is adjacent to the treatment location. The guidewire can then be withdrawn from the microcatheter. The delivery wire, together with the flow-diverting device mounted thereon or supported thereby, can then be advanced through the microcatheter and out the distal end thereof. The device can then self-expand into apposition with the inner wall of the blood vessel. Where an aneurysm is being treated, the device is placed across the neck of the aneurysm so that a sidewall of the device separates the interior of the aneurysm from the lumen of the parent artery. Once the device has been placed and detached from the delivery wire, the delivery wire and microcatheter are removed from the patient. The device sidewall can now perform a flow-diverting function on the aneurysm, thrombosing the blood in the aneurysm and leading to healing of the aneurysm.

An expandable device comprising a thin film forming a mesh can be used to treat an aneurysm. The expandable device can impede blood flow along an aneurysmal flow path between the prevailing direction of arterial flow and the interior of the aneurysm via, e.g., high pore density, small pore size and/or high material coverage across the aneurysmal flow path, and facilitate endothelial growth across the neck of the aneurysm or otherwise across the aneurysmal flow path. The expandable device can comprise a single component, low profile, high pore density flow diverter of a single material and/or of monolithic construction. The expandable device can facilitate accurate placement by requiring less foreshortening as compared to other commercially available devices, including braided devices. The expandable device can have a thickness that is small enough to enable placement in smaller blood vessels, thereby opening new areas of treatment for flow diversion.

According to some embodiments, an expandable device, such as a stent, can have a flow diverting section or other portion of the device that provides embolic properties so as to interfere with blood flow in (or into) the body space (e.g., an aneurysm) in (or across) which the device is deployed. The sidewall material coverage, porosity and/or pore size of one or more sections of the device can be selected to interfere with blood flow to a degree sufficient to lead to thrombosis of the aneurysm or other body space.

According to some embodiments, the expandable device can be configured to interfere with blood flow to generally reduce the exchange of blood between the parent vessel and an aneurysm, which can induce thrombosis of the aneurysm. A device (or a device component, such as a sidewall of a stent or a section of such a sidewall) that interferes with blood flow can be said to have a "flow diverting" property.

According to some embodiments, a porosity of the expandable device is equal to a ratio of an open surface area of the expandable device to a total surface area of the expandable device. The expandable device may comprise a plurality of struts, which form pores or cells as open areas between the struts.

The device can exhibit a porosity configured to reduce haemodynamic flow into and/or induce thrombosis within an aneurysm. The device can simultaneously allow perfusion to an adjacent branch vessel whose ostium is crossed by a portion of the device. The device can exhibit a high degree of flexibility due to the materials used, the density (i.e., the porosity) of the struts, and the arrangement of struts.

The device is self-expanding to a relaxed state or an expanded state. As used herein, the relaxed state is one to which the expandable device will self-expand in the absence of any containment or external forces. As used herein, expanded state is one to which the expandable device is capable of self-expanding, ignoring any containment, such by as a blood vessel. For example and simplicity of measurement, this expanded state can be one to which the expandable device will self-expand within a straight, non-tapering cylindrical tube with an inside diameter that is slightly smaller than the maximum diameter of the expandable device in the relaxed state.

According to some embodiments, the expandable device may include a plurality of individual struts and individual cells, as well as a first longitudinal edge and a second longitudinal edge. The first longitudinal edge and the second longitudinal edge may be connected to each other to form a substantially cylindrical shape or a circumferentially continuous shape by welding, soldering, or otherwise joining the struts or edges.

According to some embodiments in which the device is not a circumferentially continuous cylinder, the first edge and second edge may be formed, for example, by cutting a preformed, etched or laser-cut tube longitudinally along the length of the tube. Regardless of the manner of forming, the expandable device may be rolled or curled such that the first and second longitudinal edges overlap one another when the expandable device is in a compressed state and/or an expanded state. Upon release from a constraint (e.g. from within a catheter), the expandable device (when configured to be self-expanding) may spring open and attempt to assume an expanded state.

While the views provided in several of the figures (e.g., FIGS. 1A, 1E, 1F, 2A, 2B, 3A, 3B and 4) show expandable devices laid flat for ease of explanation and understanding, it will be understood that the devices can possess a tubular shape, and the laid-flat drawings presented herein depict the configuration of a sidewall of the tube. While in the tubular shape, the expandable devices can have open ends of a lumen extending through the expandable device.

According to some embodiments, an expandable device can comprise a frame and a flow-diverting mesh extending over the frame. The frame can provide structural support, and the flow-diverting mesh can provide a flow-diverting function when placed over an opening in a body vessel, such as an ostium of an aneurysm.

According to some embodiments, for example as shown in FIG. 1A, an expandable device 100 may include a proximal portion 110 and a distal portion 120. The proximal portion 110 may include one or more taper sections with cells that have a different size than the individual cells 150 of the distal portion 120. The proximal portion 110 may taper gradually towards a connection mechanism 190, or some other connection point along the expandable device 100 that connects the expandable device 100 to a delivery wire (not shown). The connection mechanism 190 permits release of the expandable device 100. The connection mechanism 190 may include, for example, an electrolytically severable region. While other types of releasable connection mechanisms are also possible (e.g. a mechanically releasable connection or a thermally or electrothermally releasable connection that can function by heating and melting a connection area), in one aspect, the connection mechanism 190 comprises a connection that corrodes or dissolves under the influence of electrical energy when in contact with an electrolyte. Where an electrolytically severable connection is employed, the expandable device 100 may generally be isolated from electric current, such that during detachment of the expandable device 100, only the electrolytically severable region of the connection mechanism 190 disintegrates in blood, and the expandable device 100 separates from a delivery wire cleanly at the electrolytically severable region, and is released into the vessel.

According to some embodiments, for example as shown in FIG. 1E, the expandable device 100 can comprise a frame 130 and a flow-diverting mesh 160 extending over the frame 130. The flow-diverting mesh 160 can be disposed on a radially outer side of the frame 130, such that the flow-diverting mesh 160 is placed against a body vessel when the expandable device 100 is in a tubular shape and expanded within the body vessel. Alternatively, the mesh 160 could be disposed on a radially inner side of the frame 130, or level with or sandwiched within the frame 130.

According to some embodiments, the frame 130 can comprise a plurality of interconnected frame struts 140 forming frame cells 150 between the frame struts 140. The frame struts 140 can form a series of undulations (e.g., sinusoidal or "S-curves") that extend longitudinally across some or all of the distal portion 120 of the expandable device 100. The frame struts 140 can be connected to each other at or near peaks or troughs thereof. The thickness and/or width of the frame struts 140 can be equal to or less than 45 μm. The thickness and/or width of the frame struts 140 can be 20 to 45 μm. Any suitable frame configuration can be employed, other than that shown in FIGS. 1A and 1E.

According to some embodiments, the flow-diverting mesh 160 can comprise a plurality of interconnected mesh struts (e.g., connector struts 170 and bridge members 180) forming mesh cells 165. The number of mesh cells 165 is greater than a number of frame cells 150. The number of mesh cells 165 can be 10 to 200 times greater than the number of frame cells 150. For example, within each frame cell 150, between 10 and 200 mesh cells 165 can be formed. While the flow-diverting mesh 160 can extend over the frame 140, mesh cells 165 are considered to be within a frame cell 150 if any portion of the mesh cells extends over or across any portion of the frame cell 150. The flow-diverting mesh 160 can provide a porosity that is lower than a porosity provided by the frame 130 alone. For example, the porosity provided by the flow-diverting mesh 160 can be in the range of 5%-95%. The mesh cells 165 can provide a pore size that is smaller than a pore size provided by the frame cells 150. A pore size can be measured via a maximum-inscribed-circle technique. The pore size provided by the mesh cells 165 can be between 2 μm and 35 μm.

According to some embodiments, the frame 130 can comprise frame cells 150 with at least two different shapes and/or sizes. According to some embodiments, the flow-diverting mesh 160 can comprise mesh cells 165 with at least two different shapes and/or sizes. According to some embodiments, the flow-diverting mesh 160 does not extend over any of the proximal portion 110.

According to some embodiments, a series of connector struts 170 can connect to each other to extend along some or all of a circumference of the expandable device 100 when the expandable device 100 forms a tubular shape. In a band or column, the struts 170 can be arranged in a "zigzag" pattern as depicted in FIGS. 1A and 1E, thereby forming a V-strut band or column. In some embodiments, the struts 170 of an individual band or column can alternate in width, e.g. between relatively wide and relatively narrow struts 170 as shown in FIG. 1E. A circumferentially extending band or column of connector struts 170 can be connected to the adjacent band(s) or column(s) of connector struts 170 by one or more bridge members 180. Some or all of the bridge members 180 can be connected to connector struts 170 at opposing longitudinal ends of the bridge members 180. As depicted in FIG. 1E, in one embodiment, the bridge members 180 extend longitudinally (but also circumferentially, to a lesser (or greater, or equal) degree than they do longitudinally) from one end connected to one adjacent connector strut 170 to an opposing end connected to another adjacent connector strut 170, with two curved sections (e.g., forming an "S" shape). Such a configuration permits elongation and foreshortening of the bridge members 170, as necessary, during compression, expansion or bending of the device 100. Instead of or in addition to such an "S" shape, one or both ends of the bridge member(s) 180 can connect to a connector strut 170 at a location that is spaced from either longitudinal end of the strut 170, e.g. in a central longitudinal region of the strut 170. The bridge member(s) 180 can therefore be made longer, and accordingly better able to elongate or foreshorten, without need to increase the distance between adjacent columns of connector struts 170. Thus the mesh can accommodate compression, expansion, elongation or bending of the device 100 during delivery and deployment. Moreover, in some embodiments, the mesh 160 is bonded or coupled to, or formed monolithically with, the frame 130 in such a manner that the struts 170 and/or bridge members 180 are immovable relative to (or secured to) the frame struts 140 along some or all of the perimeter of an individual frame cell 150 (or of some or all frame cells 150). In such an embodiment, the employment of a pattern for the mesh that can accommodate elongation, foreshortening, etc. in this manner facilitates expansion, contraction, elongation, foreshortening, distortion, etc. of the frame cells 150 as the device 100 is expanded, contracted, bent, etc. during delivery and deployment. Thus any tendency of the mesh 160 to inhibit or affect the mechanical performance of the frame 130, or for the frame to tear or distort the mesh, can be reduced or eliminated. The thickness and/or width of the connector struts 170 and/or bridge members 180 can be equal to or less than 10 µm, for example 5 µm.

FIG. 1C depicts a perspective view of a strut according to some embodiments of the subject technology. FIG. 1D depicts a cross-sectional view of a strut or bridge member according to some embodiments of the subject technology. As shown, the connector strut or bridge member has a length, a width, and a thickness. The thickness can be measured as a dimension that is orthogonal to a central axis when the expandable device 100 is considered in a tubular shape or as a dimension that is orthogonal to a plane of the expandable device 100 when represented as laid-flat. The length can be measured as a distance extending between ends of a strut, where the ends connect to another structure. The width can be measured as the distance that is generally orthogonal to the length and thickness. The width and length of a strut can contribute to a surface coverage and porosity of the expandable device 100. According to some embodiments, the strut can have a square cross-section. However, the strut may have other suitable cross-sectional shapes, such as rectangular, polygonal, round, ovoid, elliptical, or combinations thereof.

According to some embodiments, some or all of the frame struts 140 can comprise a radiopaque marker. The radiopaque marker can be disposed on a substantially straight section of a frame strut 140, so the radiopaque marker is predominantly not subject to bending or flexing. The radiopaque marker can extend from a frame strut 140 into a frame cell 150 and/or a mesh cell 165. One or more mesh struts can be omitted from a pattern to accommodate the presence of the radiopaque marker. The radiopaque marker can be formed on the frame struts 140 by a process that is the same or different than a process used to form the frame and/or the mesh, which are discussed further herein.

According to some embodiments, struts of a flow-diverting mesh can form a pattern other than that shown in FIGS. 1A and 1E. The shape and size of mesh cells can be altered while still providing a flow-diverting function when placed over an opening in a body vessel, such as an ostium of an aneurysm.

According to some embodiments, for example as shown in FIG. 2A, an expandable device 200 may include a proximal portion 210 and a distal portion 220. The proximal portion 210 may taper gradually towards a connection mechanism 290. According to some embodiments, for example as shown in FIG. 2B, the expandable device 200 can comprise a frame 230 and a mesh 260 extending over the frame 230. The frame 230 can comprise a plurality of interconnected frame struts 240 forming frame cells 250 between the frame struts 240. The mesh 260 can comprise a plurality of interconnected mesh struts (e.g., connector struts 270 and bridge members 280) forming mesh cells 265. Features of the expandable device 200 that are identified with reference numerals that differ from the reference numerals for the expandable device 100 by a multiple of 100 can have the same aspects as the corresponding features in the expandable device 100, unless noted otherwise. Any suitable frame configuration can be employed, other than that shown in FIGS. 2A-2B.

According to some embodiments, a series of connector struts 270 can connect to each other to extend along some or all of a circumference of the expandable device 200, e.g., in the form of circumferential bands or columns of struts 170, when the expandable device 200 forms a tubular shape. Mesh cells 265 formed between connector struts 270 can be approximately diamond shaped, thereby forming bands or columns of diamond shaped cells. Other mesh cells 265 formed at least in part by bridge members 280 can have a different shape (e.g., hourglass). A circumferentially extending series, band or column of connector struts 270 can be connected to another column of connector struts 270 by one or more bridge members 280. Some or all of the bridge members 280 can be connected to connector struts 270 at opposing longitudinal ends of the bridge members 280. As depicted in FIG. 2B, in one embodiment, the bridge members 280 extend longitudinally (but also circumferentially, to a lesser (or greater, or equal) degree than they do longitudinally) from one end connected to one adjacent connector strut 270 to an opposing end connected to another adjacent connecting strut 270, with two curved sections (e.g., forming an "S" shape). Such a configuration permits elongation and foreshortening of the bridge members 270, as necessary, during compression, expansion or bending of the device 200. Instead of or in addition to such an "S" shape, one or both ends of the bridge member(s) 280 can connect to a connector strut column at a location that is spaced from either longitudinal end of the column, e.g. in a central longitudinal region of the column. The bridge member(s) 280 can therefore be made longer, and accordingly better able to elongate or foreshorten, without need to increase the distance between adjacent columns of connector struts 270. Thus the mesh can accommodate compression, expansion, elongation or bending of the device 200 during delivery and deployment. Moreover, in some embodiments, the mesh 260 is bonded or coupled to, or formed monolithically with, the frame 230 in such a manner that the struts 270 and/or bridge members 280 are immovable relative to (or secured to) the frame struts 240 along some or all of the perimeter of an individual frame cell 250 (or of some or all frame cells 250). In such an embodiment, the employment of a pattern for the mesh that can accommodate elongation, foreshortening, etc. in this manner facilitates expansion, contraction, elongation, foreshortening, distortion, etc. of the frame cells 250 as the device 200 is expanded, contracted, bent, etc. during delivery and deployment. Thus any tendency of the mesh 260 to inhibit or affect the mechanical performance of the frame 230, or for the frame to tear or distort the mesh, can be reduced or eliminated.

According to some embodiments, struts of a flow-diverting mesh can form a pattern that is similar to the pattern of struts that form a frame. The shape of frame cells and mesh cells can be the same or similar, while the size of the mesh cells are substantially smaller than that of the frame cells. For example, the pattern of the flow-diverting mesh can be the same as that of the frame, but made on a smaller scale.

According to some embodiments, for example as shown in FIG. 4, an expandable device 400 may include a proximal portion 410, a first distal portion 418, a second distal portion 420 (e.g., flow diverting portion), and a third distal portion 422. The proximal portion 410 may taper gradually towards a connection mechanism 490. According to some embodiments, for example as shown in FIGS. 3A and 3B, the expandable device 300 can comprise a frame 330 and a mesh 360 extending over the frame 330. The frame 330 can comprise a plurality of interconnected frame struts 340 forming frame cells 350 between the frame struts 340. The mesh 360 can comprise a plurality of interconnected mesh struts 370 forming mesh cells 365. Features of the expandable device 300 that are identified with reference numerals that differ from the reference numerals for the expandable device 100 by a multiple of 100 can have the same aspects as the corresponding features in the expandable device 100, unless noted otherwise. Any suitable frame configuration can be employed, other than that shown in FIGS. 3A and 3B.

With reference to FIG. 4, according to some embodiments, the mesh 460 can be confined to the second distal portion 420, such that the mesh 460 does not extend over the first distal portion 418 or the third distal portion 422. The second distal portion 420 can be designed to overlie an aneurysm for flow diversion therapy, while the first distal portion 418 and/or the third distal portion 422 can overlie a branch vessel to allow perfusion thereto.

With reference to FIGS. 3A-3B, according to some embodiments, at least a portion of the mesh 360 can have the same shape as the frame 330. For example, the mesh struts 370 and the mesh cells 365 can have the same shape as the frame struts 340 and the frame cells 350, respectively. However, the mesh struts 370 and the mesh cells 365 can have a size that is different than that or the frame struts 340 and the frame cells 350, respectively. Accordingly, the pattern of the mesh 360 can be a small-scaled pattern of the frame 330. In some embodiments, the mesh 360 is bonded or coupled to, or formed monolithically with, the frame 330 in such a manner that the mesh struts 370 are immovable relative to (or secured to) the frame struts 340 along some or all of the perimeter of an individual frame cell 350 (or of some or all frame cells 350). In such an embodiment, the employment of a pattern for the mesh that is similar or identical to, but smaller in scale than, that employed for the frame permits the mesh to mimic the expansion, contraction, elongation, foreshortening, distortion, etc. of the frame cells 350 as the device 300 is expanded, contracted, bent, etc. during delivery and deployment. Thus any tendency of the mesh 360 to inhibit or affect the mechanical performance of the frame 330, or for the frame to tear or distort the mesh, can be reduced or eliminated.

According to some embodiments, the mesh struts 370 can form a series of undulations (e.g., sinusoidal or "S-curves") that extend longitudinally across the some or all of the second distal portion 320 of the expandable device 300. The mesh struts 370 can be connected to each other at or near peaks or troughs thereof.

An expandable device may be formed, for example, by laser cutting a pre-formed tube or sheet, by interconnecting components (e.g., by laser welding), by vapor deposition techniques, or combinations thereof. A frame can be formed by the same process as a mesh, or the frame can be formed by a process different than that by which the mesh is formed. The expandable device can be formed using known flexible materials such as nitinol, stainless steel, cobalt-chromium alloys, Elgiloy, magnesium alloys, tungsten, tantalum, platinum, or combinations thereof.

According to some embodiments, an expandable device can be formed by a photolithography process. A substrate can be provided with a base for supporting the formation of the expandable device. The base (e.g., copper) can be used temporarily as a buffer between the substrate and a primary material used to form the frame. After the base is provided on the substrate, the primary material is provided thereon, for example by vapor deposition. The primary material can be provided as a thin film of substantially uniform thickness. The thickness of the primary material can correspond to the desired thickness of the frame, as described herein. Portions of the primary material can be removed to form the structure of the frame. For example, a photomask, based on a strut pattern, can be used to selectively expose portions of the primary material to light and etch the primary material into the desired shape for the frame. Alternatively or in combination, a chemical agent can be used to remove the portions of the primary material that are not protected by a photoresist.

After the primary material is formed into the frame, a secondary material used to form the mesh is provided thereon, for example by vapor deposition. The secondary material can be provided as a thin film of substantially uniform thickness. The thickness of the secondary material can correspond to the desired thickness of the mesh, as described herein. Portions of the secondary material can be removed to form the structure of the mesh, while preserving the structure of the frame. For example, a photomask, based on a strut pattern, can be used to selectively expose portions of the secondary material to light and etch the secondary material into the desired shape for the mesh. Alternatively or in combination, a chemical agent can be used to remove the portions of the secondary material that are not protected by a photoresist.

The base can then be eroded to separate the expandable device (frame and mesh) from the substrate. The expandable device can be further treated to form a desired shape (e.g., tubular) and have the desired heat set and/or shape memory properties.

According to some embodiments, an expandable device can be formed by a laser cutting process. The expandable device may be formed by cutting a pattern of struts on a tube or on a flat sheet and then rolling the flat sheet into a generally tube-like or coiled shape. The expandable device in a generally tube-like or coiled shape can be circumferentially continuous or discontinuous. Where the expandable device is circumferentially discontinuous, portions of the expandable device can overlap in certain states. According to some embodiments, the frame can be formed by a laser cutting process, and the mesh can be formed on the frame by vapor deposition and photolithography, as described above.

As mentioned elsewhere herein, the present disclosure also includes methods of treating a vascular condition, such as an aneurysm, with any of the embodiments of the expandable devices disclosed herein. The expandable device could be deployed across the neck of an aneurysm and its flow-diverting properties employed to reduce blood flow between the aneurysm and the parent vessel, cause the blood inside the aneurysm to thrombose, and lead to healing of the aneurysm.

In order to implant any of the expandable devices disclosed herein, the expandable device can be mounted in a delivery system. Generally, the delivery system can include an elongate delivery wire that supports or contains the expandable device, and both components can be slidably received in a lumen of a microcatheter or other elongate sheath for delivery to any region to which the distal opening of the microcatheter can be advanced. The delivery wire is employed to advance the expandable device through the microcatheter and out the distal end of the microcatheter so that the expandable device is allowed to self-expand into place in the blood vessel, across an aneurysm or other treatment location. Accordingly, a vascular treatment apparatus can comprise a delivery system, such as any of the delivery systems described herein, and an expandable device, such as any of the expandable devices described herein, mounted in or supported by the delivery system.

A treatment procedure can begin with obtaining percutaneous access to the patient's arterial system, typically via a major blood vessel in a leg or arm. A guidewire can be placed through the percutaneous access point and advanced to the treatment location, which can be in an intracranial artery, or any neurovascular artery, peripheral artery or coronary artery. (As configured for neurovascular use, any of the expandable devices disclosed herein can have a diameter of 2-8 mm in the relaxed state or the expanded state; expandable devices used in the peripheral or coronary vasculature can have a diameter of 1-20 mm in the relaxed state or the expanded state.) The microcatheter is then advanced over the guidewire to the treatment location and situated so that a distal open end of the microcatheter is adjacent to the treatment location. The guidewire can then be withdrawn from the microcatheter and the delivery wire, together with the expandable device mounted thereon or supported thereby, can be advanced through the microcatheter and out the distal end thereof. The expandable device can then self-expand into apposition with the inner wall of the blood vessel. Where an aneurysm is being treated, the expandable device is placed across the neck of the aneurysm so that a sidewall of the expandable device separates the interior of the aneurysm from the lumen of the parent artery. Once the expandable device has been placed and detached from the delivery wire, the delivery wire and microcatheter are removed from the patient. The expandable device sidewall can now perform a flow-diverting function on the aneurysm, thrombosing the blood in the aneurysm and leading to healing of the aneurysm.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. Various methods are disclosed presenting elements of the various steps in a sample order, and are not meant to be limited to the specific order or hierarchy presented.

Furthermore, to the extent that the term "include," "have," or the like is used herein, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The following claims and their equivalents are intended to cover such forms or modifications as would fall within the scope and spirit of the present technology.

I claim:
1. A medical device comprising:
a frame including a plurality of interconnected frame struts, a plurality of first frame cells, and a plurality of second frame cells, wherein the plurality of first and second frame cells are formed between adjacent ones of the frame struts, and wherein a thickness of the frame struts is 20 μm to 45 μm; and
a mesh including a plurality of interconnected mesh struts forming a plurality of mesh cells therebetween, the plurality of mesh struts comprising first mesh struts and second mesh struts, wherein a first end of each second mesh strut is connected to one of the first mesh struts and a second end of each second mesh strut is connected to another one of the first mesh struts, the second mesh struts having an S-like shape, and the mesh struts having a thickness less than or equal to 10 μm, wherein each of the thickness of the frame struts and the thickness of the mesh struts is measured as a dimension that is generally orthogonal to a central longitudinal axis of the medical device when the medical device is in a tubular shape, wherein—
the frame and mesh comprise a monolithic metal structure,
the mesh is fixed relative to the frame,
the mesh extends across the first frame cells, the mesh cells have an area that is less than an area of the first frame cells and an area of the second frame cells, and the mesh is configured to divert the flow of a liquid.

2. The medical device of claim 1 wherein the frame struts and the mesh struts are configured to lengthen and/or shorten in response to external forces applied to the medical device.

3. The medical device of claim 1 wherein individual first mesh struts extend across a corresponding one of the first frame cells and are connected to the frame at a perimeter of the corresponding first frame cell.

4. The medical device of claim 3 wherein the frame has a circumference, and wherein the first mesh struts extend circumferentially about the frame.

5. The medical device of claim 3, wherein the second mesh struts extend longitudinally farther than they extend circumferentially.

6. The medical device of claim 3 wherein—
in a first state, the second mesh struts extend longitudinally farther than they extend circumferentially, and
in a second state, the second mesh struts extend longitudinally to a lesser degree and circumferentially to a greater degree than in the first state.

7. The medical device of claim 1 wherein the frame includes a proximal portion and a distal portion, wherein the proximal portion includes only second frame cells, and wherein the mesh does not extend across the second frame cells.

8. The medical device of claim 1 wherein—
the frame includes a proximal portion, a distal portion, and a flow-diverting portion between the distal and proximal portions,
the flow-diverting portion includes only first frame cells,
the proximal and distal portions include only second frame cells, and
the mesh does not extend across the second frame cells.

9. The medical device of claim 1 wherein between 10 and 100 mesh cells are formed within each first frame cell.

10. The medical device of claim 1 wherein the first and second frame cells comprise at least two different shapes and/or sizes.

11. The medical device of claim 1 wherein the mesh cells comprise at least two different shapes and/or sizes.

12. The medical device of claim 1 wherein a shape of some or all of the first frame cells is the same as a shape of some or all of the mesh cells.

13. The medical device of claim 1 wherein the device is sufficiently flexible to be positioned within a tortuous region of a blood vessel of a human patient.

14. The medical device of claim 1 wherein the entire mesh is fixed relative to the frame.

15. A device for diverting blood flow in a vessel, comprising:
a plurality of interconnected frame struts defining a plurality of first cells therebetween, the first cells having a perimeter, wherein a thickness of the frame struts is 20 µm to 45 µm;

a plurality of connector struts extending across at least some of the first cells, wherein individual connector struts are connected to the perimeter of a corresponding one of the first cells and have a thickness that is less than or equal to 10 µm;

a plurality of bridge struts, wherein a first end of each bridge strut is connected to one of the connector struts and a second end of each bridge strut is connected to another one of the connector struts, wherein the bridge struts have an S-like shape, and wherein the bridge struts have a thickness that is less than or equal to 10 µm, wherein each of the thickness of the connector struts, the thickness of the frame struts, and the thickness of the bridge struts is measured as a dimension that is generally orthogonal to a central longitudinal axis of the device when the device is in a tubular shape; and a plurality of second cells formed by the connector struts and the bridge struts, wherein the second cells have an area that is less than an area of the first cells, and wherein the second cells are configured to divert blood flow, wherein the frame struts, connector struts, and bridge struts comprise a monolithic structure.

16. The device of claim 15 wherein the frame struts have a generally sinusoidal-like shape and wherein the bridge struts and frame struts are configured to lengthen or shorten in response to external forces applied to the device.

17. The device of claim 15 wherein the device has a circumference, wherein the connector struts have a periodic shape and extend circumferentially, and wherein the connector struts are configured to lengthen or shorten in response to external forces applied to the device.

18. An expandable device for diverting blood flow in a vessel lumen, the expandable device comprising:
a proximal portion including a plurality of first cells;
a distal portion having a generally tube-like shape in an expanded state and including a plurality of second cells, the distal portion having a thickness of 20 pm to 45 pm; and
a mesh including a plurality of pores and extending across at least some of the second cells in the distal portion, wherein the second cells and mesh comprise a monolithic metal structure, the mesh is fixed relative to the second cells, a porosity of the mesh is less than a porosity of the distal portion and less than a porosity of the proximal portion, and the mesh is configured to divert blood from flowing through the second cells,
wherein a thickness of the mesh is less than or equal to 10 pm, and wherein each of the thickness of the mesh and the thickness of the expandable device is measured as a dimension that is generally orthogonal to a central longitudinal axis of the expandable device when at least the distal portion of the expandable device is in an expanded state;
wherein the proximal portion tapers to a connector configured to be removably coupled to a delivery wire.

* * * * *

UNITED STATES PATENT AND TRADEMARK OFFICE
CERTIFICATE OF CORRECTION

PATENT NO. : 10,893,869 B2  
APPLICATION NO. : 15/469276  
DATED : January 19, 2021  
INVENTOR(S) : Animesh Choubey Page 1 of 1

It is certified that error appears in the above-identified patent and that said Letters Patent is hereby corrected as shown below:

In the Claims

In Column 26, in Claim 18, Lines 38-39, delete "20 pm to 45 pm;" and insert -- 20 µm to 45 µm; --, therefor.

In Column 26, in Claim 18, Lines 48-49, delete "10 pm," and insert -- 10 µm, --, therefor.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*